(12) United States Patent
Wang et al.

(10) Patent No.: US 8,431,577 B2
(45) Date of Patent: Apr. 30, 2013

(54) CRYSTALLINE FORM OF ESZOPICLONE, COMPOSITION, PREPARATION AND USES THEREOF

(75) Inventors: Guocheng Wang, Tianjin (CN); Xueyu Xu, Tianjin (CN)

(73) Assignee: Tianjin Tasly Group Co., Ltd., Tianjin (CN)

( * ) Notice: Subject to any disclaimer, the term of this patent is extended or adjusted under 35 U.S.C. 154(b) by 45 days.

(21) Appl. No.: 12/999,867

(22) PCT Filed: Apr. 17, 2009

(86) PCT No.: PCT/CN2009/000414
§ 371 (c)(1),
(2), (4) Date: Dec. 17, 2010

(87) PCT Pub. No.: WO2009/152684
PCT Pub. Date: Dec. 23, 2009

(65) Prior Publication Data
US 2011/0098307 A1     Apr. 28, 2011

(30) Foreign Application Priority Data
Jun. 18, 2008    (CN) .......................... 2008 1 0053548

(51) Int. Cl.
*A61K 31/495* (2006.01)
(52) U.S. Cl.
USPC ............ 514/249; 544/350; 544/389; 546/345
(58) Field of Classification Search .................. 514/249; 544/350, 389; 546/345
See application file for complete search history.

(56) References Cited

U.S. PATENT DOCUMENTS
| | | | |
|---|---|---|---|
| 6,339,086 B1 | 1/2002 | Jerussi et al. | |
| 2002/0193378 A1 | 12/2002 | Cotrel et al. | |

FOREIGN PATENT DOCUMENTS
| | | | |
|---|---|---|---|
| CN | 1854137 A | | 11/2006 |
| CN | 101195623 A | | 6/2008 |
| EP | 2 020 403 A1 | | 2/2009 |
| EP | 2 058 313 A2 | | 5/2009 |
| WO | WO 2007/083188 A2 | | 7/2007 |
| WO | WO 2007/088073 A1 | | 8/2007 |
| WO | WO 2007/124025 A2 | | 11/2007 |
| WO | WO 2008/126105 A2 | | 10/2008 |

OTHER PUBLICATIONS

R.J. Terblanche et al., "Characterization of Zopiclone Crystal Forms Found Among Generic Raw Materials," Drug Development and Industrial Pharmacy, 26(5), 2000, pp. 531-537.
Extended European Search Report, 09765324.0-2101/2301938 PCT/CN2009000414.
"Enzymatic Resolution of New Carbonate Intermediates for the Synthesis of (s)-(+)-Zopiclone", Solares, et al., Tetrahedron: *Assymmetry* 13 (2002) 2577-2582.

*Primary Examiner* — Douglas M Willis
(74) *Attorney, Agent, or Firm* — Brinks Hofer Gilson & Lione (57) ABSTRACT

The present invention discloses a crystalline form of S-zopiclone (Formula I) having a powder X-Ray diffraction spectrum excited by Cu-Ka radiation with characteristic peaks expressed in terms of 2θ at about 11.08°, about 12.38°, about 15.86°, about 17.88°, about 19. 98° and about 20.58°; a DSC thermogram with a peak at about 207.7° C. and an infrared absorption spectrum (IR) with characteristic peaks at about 3078 $cm^{-1}$, about 2942~2838 $cm^{-1}$, about 2790 $cm^{-1}$, about 1716 $cm^{-1}$, about 1463 $cm^{-1}$, about 1372 $cm^{-1}$ and about 757 $cm^{-1}$. The present invention also discloses a method for preparing the crystalline form of eszopiclone, its pharmaceutical composition and its use in preparing a medicament for treating sleep disorders.

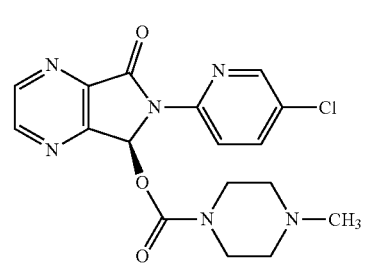

(I)

8 Claims, 8 Drawing Sheets

CRYSTALLINE FORM OF ESZOPICLONE, COMPOSITION, PREPARATION AND USES THEREOF

The present application is the national phase application of PCT Application No. PCT/CN2009/000414, filed Apr. 17, 2009, which claims priority to Chinese Patent Application No. 200810053548.7, filed Jun. 18, 2008, the entireties of both of which are hereby incorporated by references.

TECHNICAL FIELD OF INVENTION

The present invention relates to the field of medicine, in particular to a crystalline form of eszopiclone and a composition, and a preparative process and a medicinal use thereof.

BACKGROUND OF INVENTION

Zopiclone, a medicine used for treatment of sleep disorder, was developed by RHONE-PONLENC RORER PHARMACEUTICAL COMPANY LTD, FRANCE in the mid-80s of the last century, and commercialized in more than 80 countries such as those countries in Europe under a trade name of IMOVANE®. The sales volume of this drug reached about 160 millions US$ in 1999, and had been used in China for nearly 10 years. Now, there are a lot of manufacturers producing it, including Shanghai Huashi Pharmaceutical Co., Ltd, Qilu Pharmaceutical Co., Ltd, and Guangdong Shunfeng Pharmaceutical Co., Ltd. The zopiclone is represented by a formula below:

Racemic zopiclone

Eszopiclone

S-zopiclone (Eszopiclone) is one chirally dextrorotatory monomer of zopiclone, having a chemical name of (+)-(S)-(4-methylpiperazine-1-carboxylate)(6-(5-chloropyridinyl-2-yl)-7-carbonyl-6,7-dihydro-5-H-pyrrolo[3,4-b]pyrazin-5-yl ester). Since 1998, it was developed by Sepracor Inc., and approved by FDA to sale in market in October 2004. However, there are a lot of severe side effects exhibited in the racemic zopiclone, including a bitter taste in mouth caused by secretion of the drug in saliva, dry mouth, drowsiness, morning fatigue, headache, dizziness and neuromotor function injury. Compared with the racemic zopiclone, the S-isomer thereof offers obvious advantages with fewer side effects. As revealed in a pharmacodynamics research, the dextrorotatory enantiomer of zopiclone significantly contributes to its short-term hypnotic effect, hence having a better effect than that of the racemic zopiclone. Meanwhile, S-zopiclone has been proved to show a low toxicity than that of the racemic zopiclone, as reported by a comparative acute toxicity research. In contrast to the racemic zopiclone, an administration of the S-isomer can have an effect of anti-anxiety without affecting sport coordination ability. Zopiclone is reported to be stereoselective against a benzodiazepine receptor, wherein the S-isomer possesses approximately 50-fold higher binding affinity to the benzodiazepine receptor than that of the R-isomer.

It is well-known that a compound, such as a drug, can often exist in different crystalline forms, which is called polymorphism. Generally speaking, different crystalline forms of the same drug can have different physical properties and chemical stabilities. It is quite important to use a drug having a definite crystalline form as a bio-active component during a manufacture of pharmaceutical preparations, which will not only exert its therapeutical effects, but also effectively reduce its toxicity and side effects. Up to now, no descriptions about a definite crystalline form of S-zopiclone have been reported among those published preparative methods and applications of its composition.

CONTENTS OF THE INVENTION

An objective of the present invention is to provide a stable crystalline form of S-zopiclone.

A further objective of the present invention is to provide a method for preparing the crystalline form of S-zopiclone.

Another objective of the present invention is to provide a composition comprising the crystalline form of S-zopiclone.

Another objective of the present invention is to provide a medical use of the crystalline form of S-zopiclone.

Figure 1:
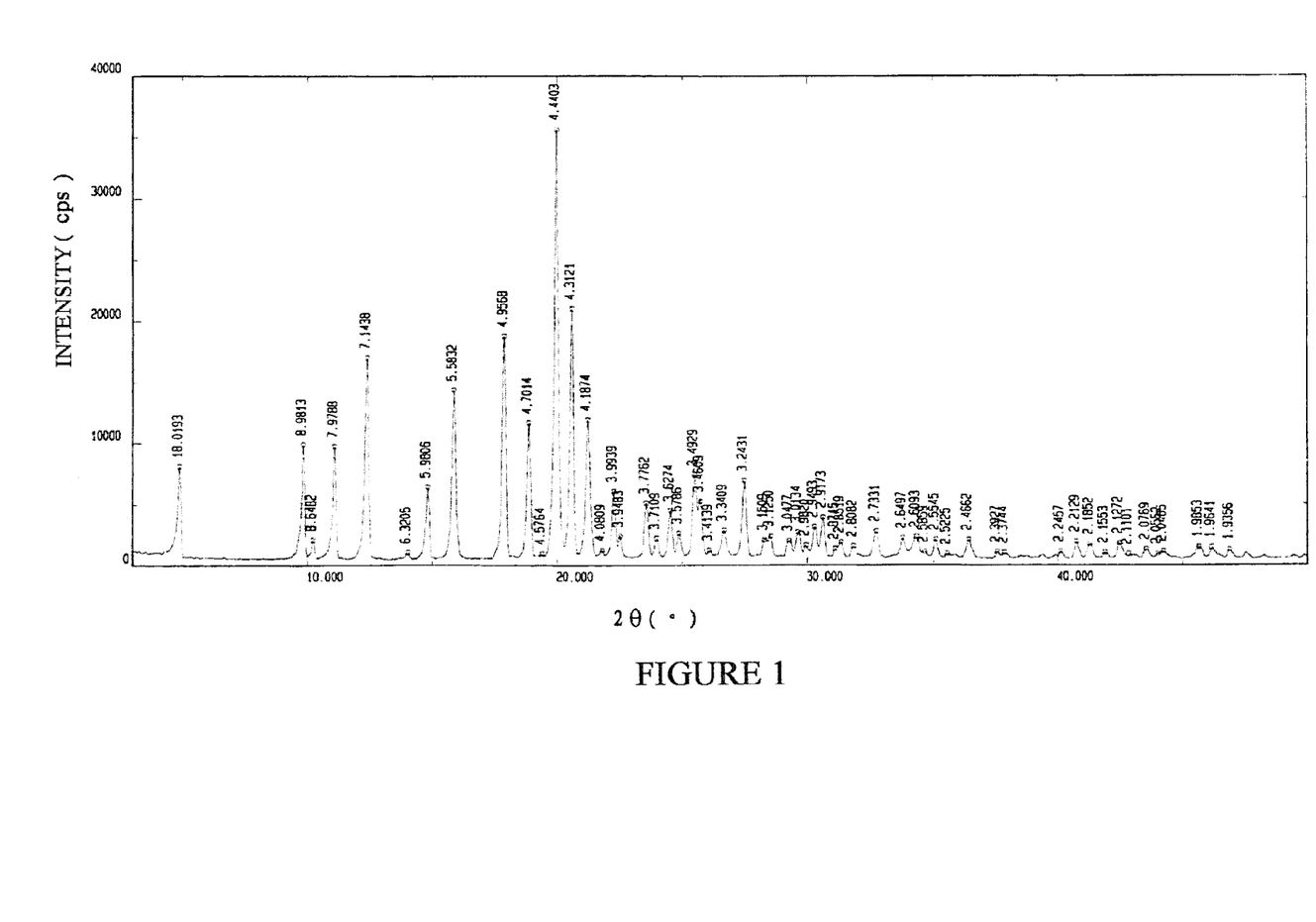
FIG. 1 presents an X-ray diffraction spectrum of the crystalline form S-zopiclone of the present invention.
Figure 2:
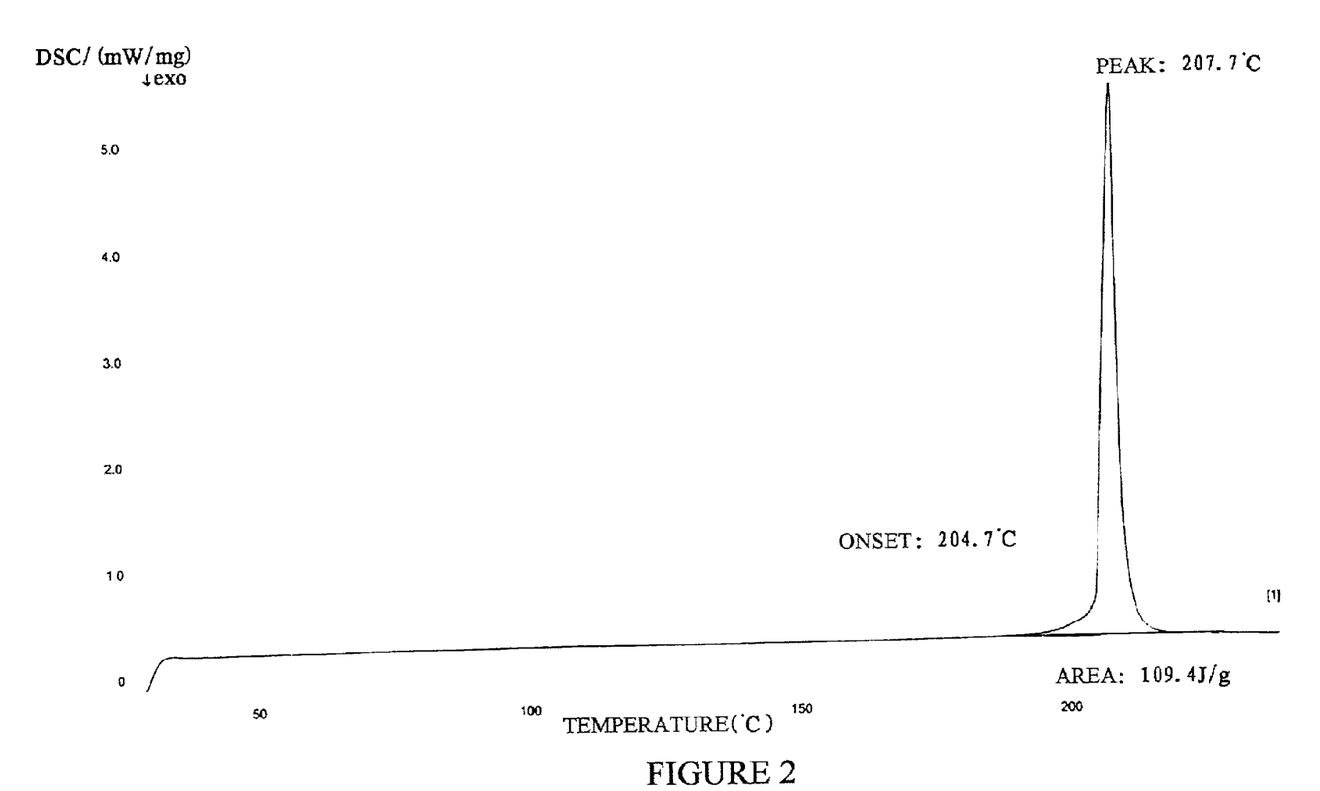
FIG. 2 presents a graph of DSC of the crystalline form of S-zopiclone of the present invention.
Figure 3:
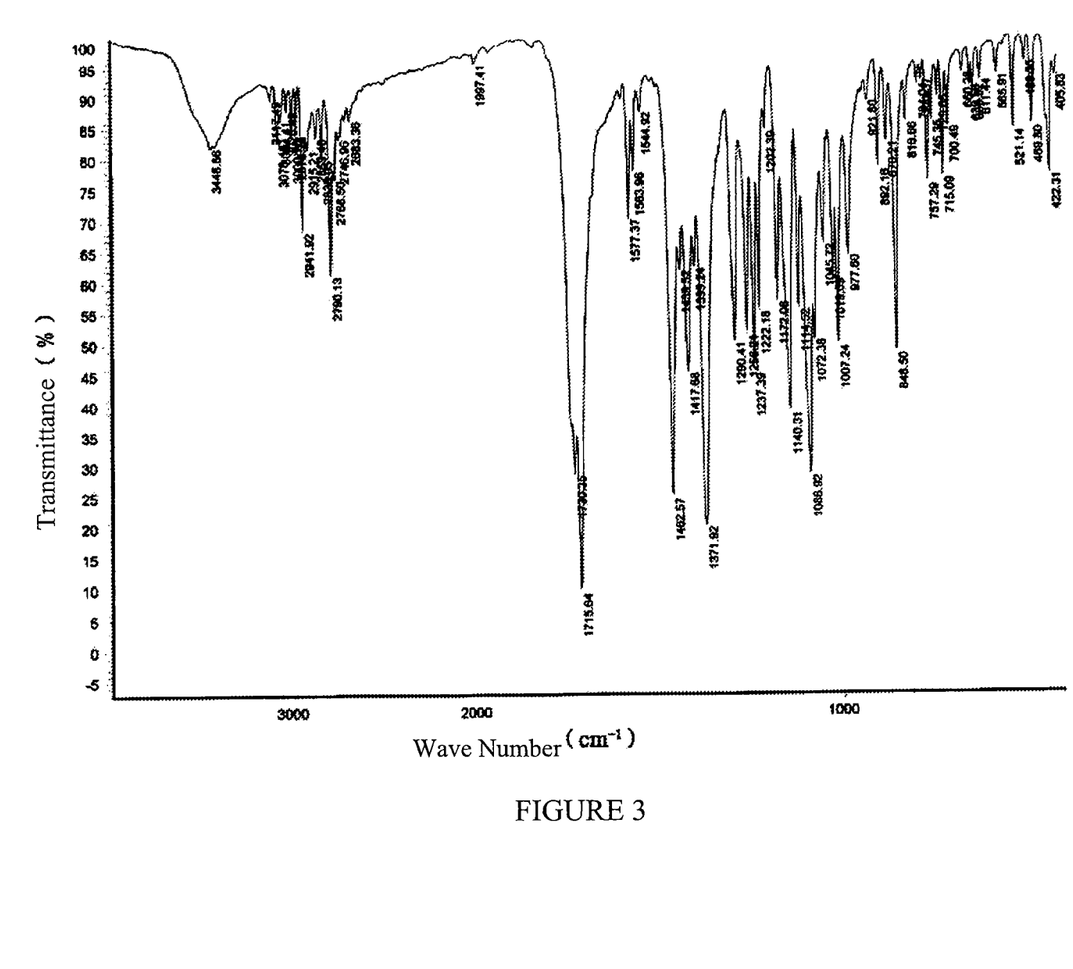
FIG. 3 presents an infrared absorption spectrum of the crystalline form of S-zopiclone of the present invention.

According to one aspect of the present invention, a crystalline form of S-zopiclone is provided, which is identified with a powder X-ray diffraction spectrum, a differential scanning calorimetry (DSC) and an infrared absorption spectrum (IR) clearly illustrated in the drawings, respectively. Relevant data are presented as follows:

A peak of DSC thermogram is at about 207.7° C.

Its powder X-ray diffraction spectrum shows characteristic peaks expressed in terms of 2θ in its average value (θ refers to the glancing angle) at about 11.08°, about 12.38°, about 15.86°, about 17.88°, about 19.98° and about 20.58°.

Its infrared absorption spectrum (IR) shows characteristic peaks at about 3078 $cm^{-1}$, about 2942~2838 $cm^{-1}$, about 2790 $cm^{-1}$, about 1716 $cm^{-1}$, about 1463 $cm^{-1}$, about 1372 $cm^{-1}$, and about 757 $cm^{-1}$, preferably at about 3078 $cm^{-1}$, about 2942~2838 $cm^{-1}$, about 2790 $cm^{-1}$, about 1716 $cm^{-1}$, about 1577~1545 $cm^{-1}$, about 1463 $cm^{-1}$, about 1372 $cm^{-1}$, about 1007 $cm^{-1}$, about 849 $cm^{-1}$ and about 757 $cm^{-1}$.

The crystalline form of S-zopiclone of the present invention is characterized by well-recognized methods of X-ray diffraction spectrum, differential scanning calorimetry (DSC) and infrared absorption spectrum (IR).

Generally, a powder X-ray diffraction spectrum obtained from a crystalline form compound is characteristic for a given crystalline form, expressed in terms of 2θ by using Cu-Kα radiation.

DSC is known to those skilled in the art, which is used to measure the thermal transition temperature when absorbing or releasing heat due to crystalline form structure change or crystalline form melting. In the continuous analysis, the difference between thermal transition temperature and melting point is typically within a range of about ±2° C., typically within a range of about ±1° C. Hence, a compound with a specific DSC peak or melting point means that its difference between DSC peak and melting point is within a range of ±2° C., which is regarded as an alternative method for identifying different crystalline forms of S-zopiclone. That is to say, a preliminary identification for different crystalline forms of a compound can be made depending on (at least partially) characteristically different transition temperature.

Infrared absorption spectrum (IR) is used for measuring absorption of infrared light caused by specific chemical bonds relating to infrared vibrating groups in a molecule.

Both DSC and IR can provide information about physicochemical properties of the crystalline form of S-zopiclone.

The process for preparing S-zopiclone, which is used as a raw material for preparing the crystalline form of S-zopiclone of the present invention, comprises:

Contacting the racemic zopiclone and D-(+)-malic acid with a mixture of methanol and acetone to dissolve under agitation at 20~30° C., cooling to 0~10° C. and maintaining the temperature for about 6~48 hours, continuing to agitate, filtering, washing with methanol and drying to obtain D-(+)-malic acid-S-zopiclone. Subsequently, the afore-obtained D-(+)-malic acid-S-zopiclone is dissolved in water. The pH value of the solution is adjusted to 6~9, then the solution is extracted with ethyl acetate, dried, concentrated and filtered to give a filter cake. The filter cake is washed and dried to obtain S-zopiclone as a raw material.

For those skilled in the prior arts, it is hard to predict whether a crystalline form of a compound is formed or not, which is associated closely with its preparation conditions. During purifying process for S-zopiclone, ethyl acetate used as a solvent for crystallization offers a lot of advantages: a reduced toxicity, a simplified operation, a lowered cost and an improved yield. Therefore, the inventors had sufficiently investigated different conditions for crystallization by using ethyl acetate as a solvent.

According to one aspect of the present invention, a method for crystallizing S-zopiclone is provided, which comprises the following steps:

(a). Dissolving S-zopiclone in ethyl acetate at a temperature ranging from 60° C. to a reflux temperature. 10~80 mL of ethyl acetate is used based on 1 g of S-zopiclone, preferably 25~50 mL ethyl acetate based on 1 g of S-zopiclone;

(b). Allowing the solution to cool down at ambient temperature to 30~50° C., preferably 35~45° C.; maintaining the temperature for 10 minutes~12 hours, preferably 1~6 hours;

(c). Continuously cooling down to 10~10° C., preferably 5~-5° C.; maintaining the temperature for 10 minutes~12 hours, preferably 1~6 hours; and (d). Separating a crystalline form.

Wherein, the crystallization method can be carried out with or without an aid of an agitation device, preferably with an aid of an agitation device.

According to one aspect of the present invention, a pharmaceutical composition comprising a therapeutically effective amount of the crystalline form of S-zopiclone of the present invention and a pharmaceutically acceptable carrier is provided. Optionally, the composition is formulated into a complex preparation with other active ingredients.

According to one aspect of the present invention, the pharmaceutical composition of the present invention is formulated into a unit-dose pharmaceutical preparation. Further, the unit-dose pharmaceutical preparation refers to a unit of the dosage-form, for example each tablet of tablets, each capsule of capsules, each bottle of oral liquids and each bag of granules, etc.

According to one aspect of the present invention, the pharmaceutical preparation can contain 0.1~99.9 wt % of the crystalline form of S-zopiclone of the present invention together with a pharmaceutically acceptable carrier. Preferably, the weight percentage of the crystalline form of S-zopiclone of the present invention in the preparation is 0.1~20 wt %, most preferably 1~10 wt %.

Generally, the crystalline form of S-zopiclone of the present invention and a pharmaceutically acceptable carrier can be used to formulate the pharmaceutical composition of the present invention by standard pharmaceutical techniques, for example by means of conventional mixing, granulating and tableting processes. It is well-known to those skilled in the prior arts that the types and characteristics of the pharmaceutically acceptable carrier are dependent upon the amount of active ingredient which is mixed with the carrier, the route of administration chosen and other known factors. Said pharmaceutically acceptable carrier according to the present invention includes various types of organic or inorganic carriers that can be administrated in combination with the composition, for example those carriers used for solid preparations such as excipients, lubricants, binding agents, disintegrants and coating agents, and pharmaceutically acceptable additives such as colorants and sweetening agents can also be applied. According to one aspect of the present invention, the pharmaceutically acceptable carriers are selected from the group consisting of sugars, such as maltose, glucose, fructose, dextran, sucrose, lactose, cyclodextrins (e.g. β-cyclodextrin), starch, celluloses and their derivatives; sugar alcohols, such as mannitol, sorbitol and xylitol; inorganic acids, such as hydrochloric acid, sulfuric acid and phosphoric acid; inorganic salts, such as sodium chloride, potassium chloride, sodium pyrosulfite, sodium hydrogen sulfite, sodium thiosulfate, calcium carbonate, calcium bicarbonate, carbonates and phosphates of alkali metals or aqueous solutions thereof; amino acids, such as glycine, methionine and cysteine hydrochloride; organic salts, such as EDTA disodium, EDTA calcium sodium, sodium lactate, stearate (such as calcium stearate and magnesium stearate) and alginate; and additionally other pharmaceutically acceptable carriers, such as mercapto acetic acid, acetic acid, vitamin C, silicon derivatives, gelatin, PVP, glycerin, tween-80, agar, surfactants, PEG, phospholipids, kaolin and talc powder, etc.

According to one aspect of the present invention, the pharmaceutically acceptable composition containing the crystalline form of S-zopiclone of the present invention can be made into preparations in any pharmaceutically acceptable dosage form, comprising tablets such as sugar-coated tablets, film-coated tablets and enteric-coated tablets; capsules such as hard capsules and soft capsules; oral liquids, buccals, granules, instant granules, pills, pulvis, pastes, pellets, suspensions, powders, solutions, injections, suppositories, ointments, plasters, creams, sprays, drops and patches. Wherein, the preparation of the present invention is preferably in oral dosage form, for example capsules, tablets, oral liquids, granules, pills, pulvis and pellets etc; and injections, for example powder injections, injection solutions and intravenous drip solutions, most preferably tablets.

According to one aspect of the present invention, the oral dosage form of the stable crystalline form of S-zopiclone can contain conventional excipients, binding agents, bulking agents, diluents, tableting agents, lubricants, disintegrants, colorants, flavoring agents, sweetening agents, and wetting agents, and, if desired, the tablets can be coated.

Preferably, the excipients can be exemplified by lactose, D-mannitol, D-sorbitol, starch (for example α-starch, amylopectin, and dextrin), celluloses and their derivatives (for example crystalline form cellulose, low-substituted hydroxypropyl cellulose, and sodium carboxymethyl cellulose), arabic gum, light anhydrous silicic acid, synthetic aluminium silicate and magnesium aluminum silicate, etc.

Preferably, the lubricants can be exemplified by magnesium stearate, calcium stearate, talc powder and silica gel, etc.

Preferably, the binding agents can be exemplified by starch (for example the α-starch, dextrin and amylopectin), sucrose, trehalose, gelatin, arabic gum, celluloses and their derivatives (for example methyl cellulose, carboxymethyl cellulose, sodium carboxymethyl cellulose, crystalline form cellulose, hydroxypropyl cellulose and hydroxypropyl methyl cellulose), D-mannitol and pyrrolidone, etc.

Preferably, the disintegrants can be exemplified by lactose, starch, sodium carboxymethyl starch, celluloses and their derivatives (for example carboxymethyl cellulose, calcium carboxymethyl cellulose and low-substituted hydroxypropyl cellulose) and light anhydrous silicic acid, etc.

Preferably, the coating agents can be exemplified by hydroxypropyl methyl cellulose, hydroxypropyl cellulose, ethyl cellulose, carboxymethyl cellulose and polyvinyl alcohol, etc.

Preferably, the colorants can be exemplified by water-soluble edible tartrazine yellow dye (edible dyes, for example the edible red No. 2 and No. 3, the edible yellow No. 4 and No. 5, the edible blue No. 1 and No. 2), water-insoluble precipitated dye (for example the aluminum salt of aforesaid water-soluble edible tartrazine yellow dye), natural dyes (for example β-carotene, chlorophyll and colcothar), etc.

Preferably, the sweetening agents can be exemplified by saccharin sodium, dipotassium glycyrrhizate, aspartame and stevia, etc.

According to one aspect of the present invention, the pharmaceutical composition can be administrated conveniently to a subject by any administration route, for example orally, locally, parenterally or inhalantly, preferably orally.

According to one aspect of the present invention, when used for treating sleep disorder, one dosage unit of the pharmaceutical composition contains 1~15 mg of the crystalline form of S-zopiclone, preferably contains 3~12 mg of the crystalline form of S-zopiclone.

According to one aspect of the present invention, a usage and dosage of the pharmaceutical composition is determined upon the condition of patient when using the composition of the present invention, it can be taken once daily and 1~10 dosage-units each time, for example before sleep, taking 1~10 bags, or 1~10 pills, or 1~10 tablets.

According to one aspect of the present invention, a use of the crystalline form of S-zopiclone of the present invention in preparing a medicament for treating sleep disorder is provided. The pharmacodynamics results are shown herein below.

Test 1 Pharmacodynamics results of the crystalline form of S-zopiclone of the present invention Different from the structure of benzodiazepine drug, S-zopiclone is found to act on a different binding site of the benzodiazepine receptor in the GABAA receptor/Cl channel complex.

As a drug to be tested, the crystalline form of S-zopiclone of the present invention was prepared in accordance with Example 1 of the present invention.

1. In Vitro Pharmacodynamics Test of the Crystalline Forms of S-Zopiclone

The $IC_{50}$ value of binding S-zopiclone with the benzodiazepine receptor is 21±3 (nmol/L), wherein the $IC_{50}$ value refers to the half maximal inhibitory concentration, which is inversely proportional to the receptor binding capacity. Thus, it indicates that S-zopiclone has a strong binding affinity with the receptor. As shown in studies, although the chemical structure of S-zopiclone is different from that of the benzodiazepine drug, both of them have a similar acting mechanism of binding the benzodiazepine receptor, but their binding sites are different.

2. In Vitro Pharmacodynamics Test of the Crystalline Form of S-Zopicolne

Male Long-Evans rats (weighing 250~275 g) were adopted, divided into 3 groups, and fed in a 12-hour light-dark cycle. After one week of feeding, the experiment was carried out.

2.1 Test of Spontaneous Activity

Horizontal activity of rats had been observed under an open circumstance to measure a total spontaneous activity. Respectively, all animals were placed into 8 black light-proof rooms, and their spontaneous activities were monitored by an infrared sensor mounted on the wall at equal intervals to record once every 10 minutes for 120 minutes.

The crystalline form of S-zopiclone was administrated to the animals at a dose of 10 mg/Kg body weight. 30~60 minutes after administration, the inhibitory effect on the locomotor ability reached a peak, and disappeared after 2 hours.

2.2 Maze Test

Administration of the crystalline form of S-zopiclone at 10 mg/Kg body weight had significant effect on total entries, open arm entries and close arm entries. At both the doses of 5 mg/Kg body weight and 10 mg/Kg body weight, it shows that the crystalline form of S-zopiclone can significantly increase residence time in the open arm.

As shown in the aforesaid results, the crystalline form of S-zopiclone showed a substantial effect not only on treating sleep disorder, but also on treating anti-anxiety without affecting sport coordination ability.

Test 2 Properties and Stability Study of the Crystalline Form of S-Zopiclone

The product was white or off-white crystal or crystalline form powder.

1. Solubility

Solubility test had been carried out by common solvents in accordance with the method of the GENERAL NOTICE in *Chinese Pharmacopoeia* (2000 Edition).

As a drug to be tested, the crystalline form of S-zopiclone of the present invention was prepared in accordance with Example 1 of the present invention.

Test method: an appropriate amount of fine powder of the crystalline form of S-zopiclone was weighed accurately, into which a certain amount of solvent was added with an accuracy of ±2%. At a temperature of 25±2° C., the solution was shaken violently for 30 seconds, which is repeated at 5-minute intervals. The solubility behavior within 30 minutes had been observed. The results were set forth in Table 1.

TABLE 1

Solubility of the crystalline form of S-zopiclone of the present invention

| Solvents | Weight of the sample (mg) | Required amount of the solvent (mL) | Required amount of the solvent for dissolving 1 g of the sample (mL) | Solubility |
|---|---|---|---|---|
| chloroform | 100 | 0.6 | 6 | freely soluble |
| hydrochloric acid(0.1 mol/L) | 10 | 0.7 | 70 | Soluble |
| acetone | 10 | 2.0 | 200 | slightly soluble |
| methanol | 10 | 5.0 | 500 | slightly soluble |
| ethyl acetate | 10 | 6.0 | 600 | slightly soluble |
| ethanol | 10 | 15.0 | 1500 | very slightly soluble |
| anhydrous ether | 10 | 90.0 | 9000 | very slightly soluble |
| water | 10 | 200 | 20000 | practically insoluble |

Conclusions

The crystalline form of S-zopiclone of the present invention are freely soluble in chloroform, soluble in hydrochloric acid (0.1 mol/L), slightly soluble in acetone, ethyl acetate or methanol, very slightly soluble in ethanol and ether, and practically insoluble in water.

2. Stability

As a drug to be tested, the crystalline form of S-zopiclone of the present invention was prepared in accordance with Example 1 of the present invention.

2.1 High Temperature (60° C.) Test

The crystalline form of S-zopiclone of the present invention was introduced into an open and colorless transparent weighing-bottle batch by batch, and placed in a thermostat container (60° C.) for 10 days. The specimens were sampled on the $5^{th}$ and $10^{th}$ day respectively to measure their stability in accordance with the key stability-relevant items. The results are set forth in Table 3.

Figure 4:
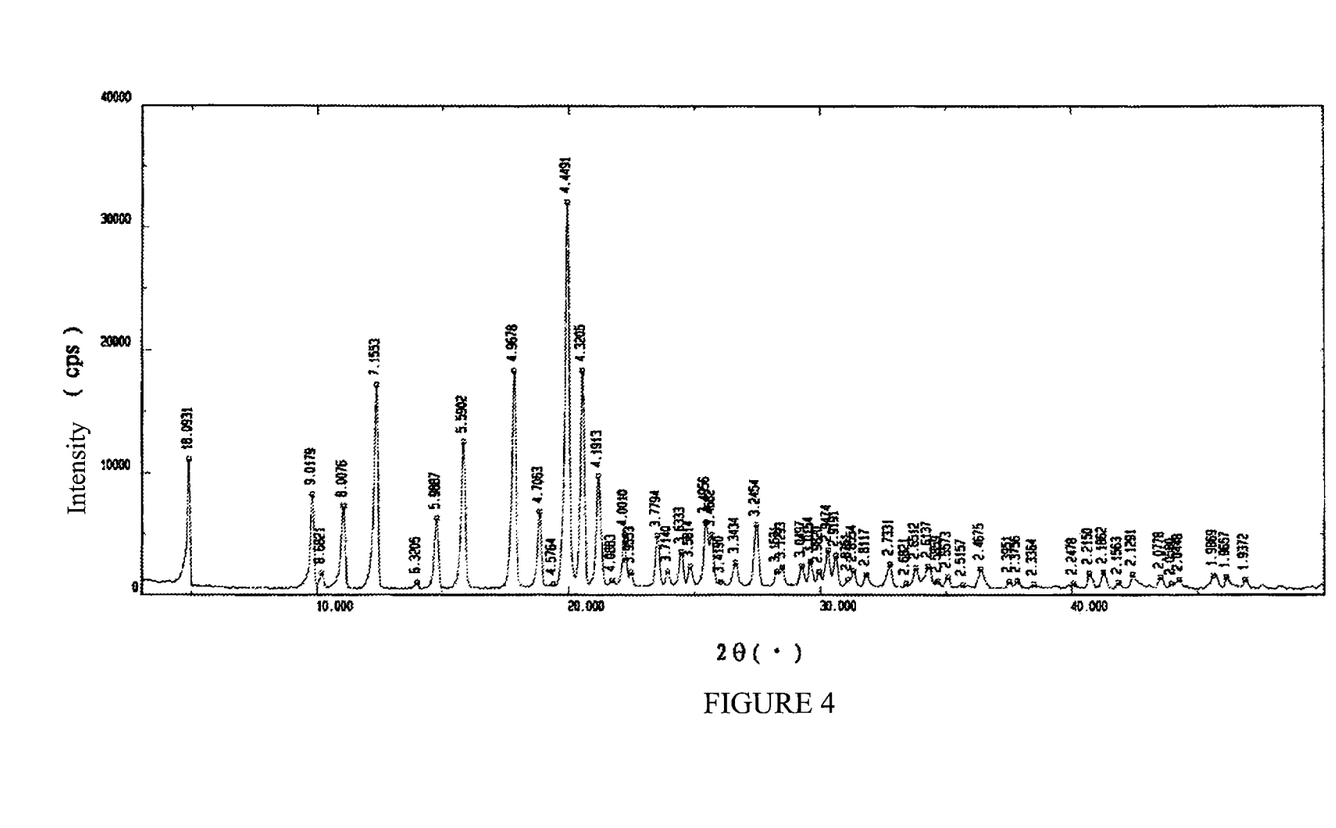
FIG. 4 presents an X-ray diffraction spectrum of the crystalline form of S-zopiclone of the present invention subjected to high temperature (60° C.) for 10 days.

As shown in the results, the crystalline form of S-zopiclone is stable after 10 days of high-temperature (60° C.), and its parameters were almost consistent with those of $0^{th}$ day, including character, melting point, and contents of related substances such as levozopiclone. The X-ray diffraction spectrum of the crystalline form of S-zopiclone of the present invention subjected to high temperature for 10 days is presented in FIG. 4.

2.2 High Humidity (25° C., RH: 92.5%) Test

The crystalline form of S-zopiclone of the present invention was introduced into an open and colorless transparent weighing-bottle batch by batch, and placed in a closed vessel ($KNO_3$ saturated solution, RH: 92.5%) for 10 days. The specimens were sampled on the 5th and 10th day respectively to measure their stability in accordance with the key stability-relevant items. Meanwhile, the weight of the tested drug pre-and post test was measured accurately. The results are set forth in Table 2 and Table 3.

Figure 5:
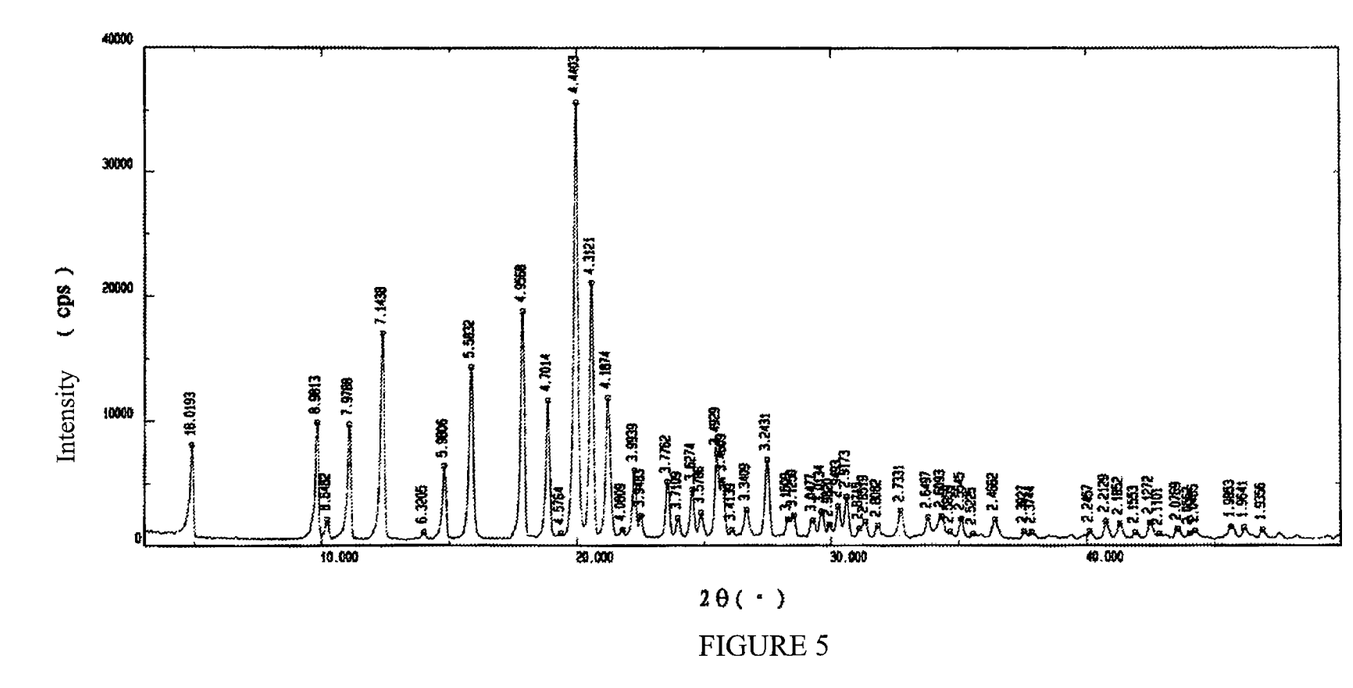
FIG. 5 presents an X-ray diffraction spectrum of the crystalline form of S-zopiclone of the present invention subjected to high humidity (25° C., relative humidity 92.5%) for 10 days.

As shown in the results, a little weight gain is observed in the crystalline form of S-zopiclone after 10 days of high-humidity, which was almost consistent with that of 0th day. The results are set forth in Table 2. The X-ray diffraction spectrum of the crystalline form of S-zopiclone subjected to high humidity for 10 days is presented in FIG. 5.

TABLE 2

Weight gain of the crystalline form of S-zopiclone in the high humidity test

| | Time | | |
|---|---|---|---|
| | $0^{th}$ day | 5th day | 10th day |
| Weight | 1.0001 g | 1.0007 g | 1.0008 g |
| Weight gain | — | 0.07% | 0.08% |

2.3 Strong Light Exposure Test

The crystalline form of S-zopiclone of the present invention was introduced into an open and colorless transparent weighing-bottle, and directly exposed to strong light (4500±500 Lx) for 10 days. The specimens were sampled on the 5th and 10th day respectively to measure their stability in accordance with the key stability-relevant items. The results are set forth in Table 3.

Figure 6:
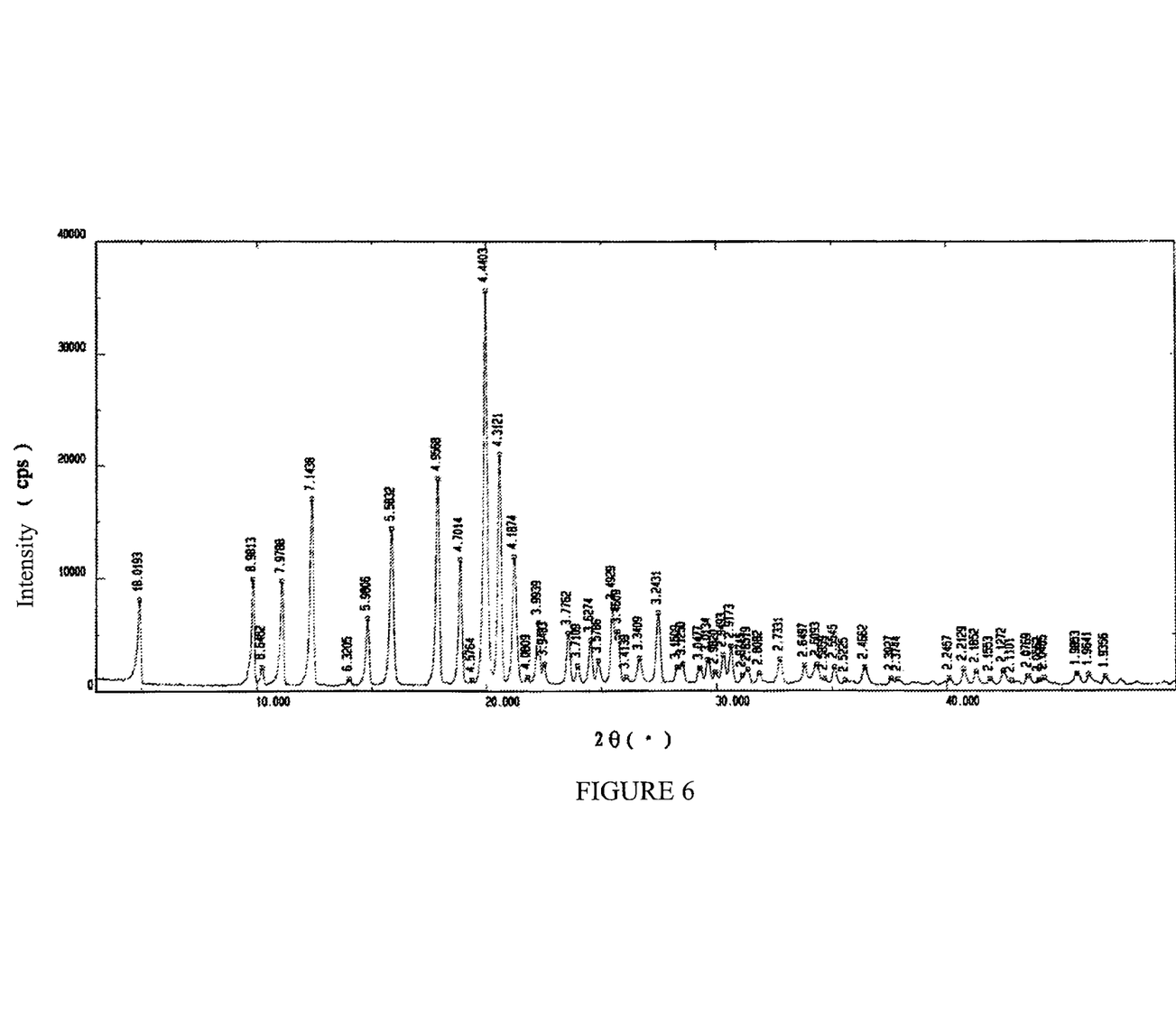
FIG. 6 presents an X-ray diffraction spectrum of the crystalline form of S-zopiclone of the present invention exposed to strong light (4500±500Lx) for 10 days.

As shown in the results, the crystalline form of S-zopiclone remained stable after 10 days of strong light exposure (4500±500 Lx), and its parameters were almost consistent with those of 0th day, including character, melting point, and contents of related substances such as levozopiclone. The X-ray diffraction spectrum of the crystalline form of S-zopiclone exposed to strong light (4500±500Lx) for 10 days is presented in FIG. 6.

TABLE 3

Test results of the influencing factors of the crystalline form of S-zopiclone

| Conditions | Time (day) | Appearance and color | Melting point (° C.) | Related substances (%) Levozopiclone | Other impurities | Content (%) |
|---|---|---|---|---|---|---|
| High temperature (60° C.) | 0 | Off-white crystalline powder | 205.5~207.0 | 0.06 | 0.09 | 100.06 |
| | 5 | Off-white crystalline powder | 206.0~207.0 | 0.08 | 0.11 | 100.01 |
| | 10 | Off-white crystalline powder | 206.0~207.0 | 0.07 | 0.12 | 100.12 |

TABLE 3-continued

Test results of the influencing factors of the crystalline form of S-zopiclone

| Conditions | Time (day) | Appearance and color | Melting point (° C.) | Related substances (%) Levozopiclone | Other impurities | Content (%) |
|---|---|---|---|---|---|---|
| High humidity (92.5%) | 0 | Off-white crystalline powder | 205.5~207.0 | 0.06 | 0.09 | 100.06 |
| | 5 | Off-white crystalline powder | 206.0~207.0 | 0.08 | 0.11 | 99.86 |
| | 10 | Off-white crystalline powder | 206.0~207.0 | 0.07 | 0.11 | 99.91 |
| Strong light exposure | 0 | Off-white crystalline powder | 205.5~207.0 | 0.06 | 0.09 | 100.06 |
| | 5 | Off-white crystalline powder | 205.5~207.0 | 0.08 | 0.10 | 99.77 |
| | 10 | Off-white crystalline powder | 205.5~206.5 | 0.07 | 0.11 | 100.02 |

2.4 Accelerated Test

The crystalline form of S-zopiclone was packaged in packages simulated the commercial ones, and placed in a thermostat container (temperature: 40±2° C., RH:75±5%) for 6 months. The specimens were sampled on the 1st, 2nd, 3rd and 6th month respectively to measure their stability in accordance with the key stability-relevant items. The results are set forth in Table 4.

Figure 7:
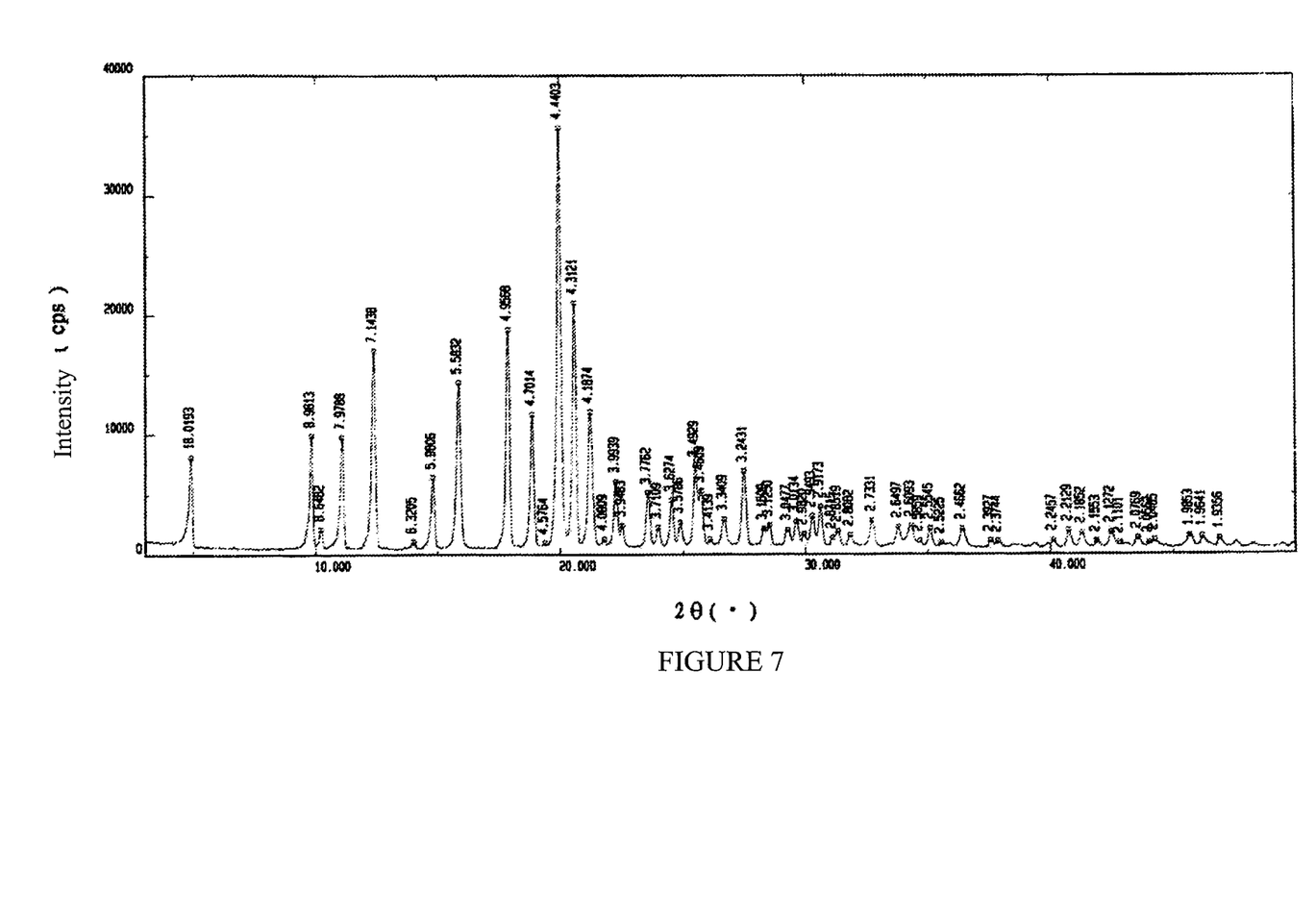
FIG. 7 presents an X-ray diffraction spectrum of the crystalline form of S-zopiclone of the present invention in a circumstance with a temperature of 40±2° C. and a relative humidity of 75±5% for 6 months.

As shown in the results, the crystalline form of S-zopiclone remained stable after 6 months of accelerated test. Its parameters were almost consistent with those of 0th day, including character, melting point, and contents of related substances such as levozopiclone. The X-ray diffraction spectrum of the crystalline form of S-zopiclone in a circumstance with a temperature of 40±2° C. and a relative humidity of 75±5% for 6 months is presented in FIG. 7.

TABLE 4

Results of the accelerated test of the crystalline form of S-zopiclone

| Time (Month) | Appearance and color | Melting point (° C.) | Related substances (%) Levozopiclone | Other impurities | Content (%) |
|---|---|---|---|---|---|
| 0 | Off-white crystalline powder | 205.5~207.0 | 0.06 | 0.09 | 100.06 |
| 1 | Off-white crystalline powder | 206.0~207.5 | 0.07 | 0.10 | 100.13 |
| 2 | Off-white crystalline powder | 206.0~207.0 | 0.07 | 0.12 | 100.02 |
| 3 | Off-white crystalline powder | 206.0~207.0 | 0.05 | 0.12 | 99.91 |
| 6 | Off-white crystalline powder | 205.5~207.0 | 0.06 | 0.09 | 99.73 |

2.5 Long-Term Reserved-Sample Test

The crystalline form of S-zopiclone was packaged in packages simulated the commercial ones, and placed at room temperature. The specimens were sampled on the 3rd, 6th, 9th, 12th, 18th, 24th, and 36th month respectively to measure their stability in accordance with the key stability-relevant items. Compared with the data on the 0th day, the results are set forth in Table 5.

Figure 8:
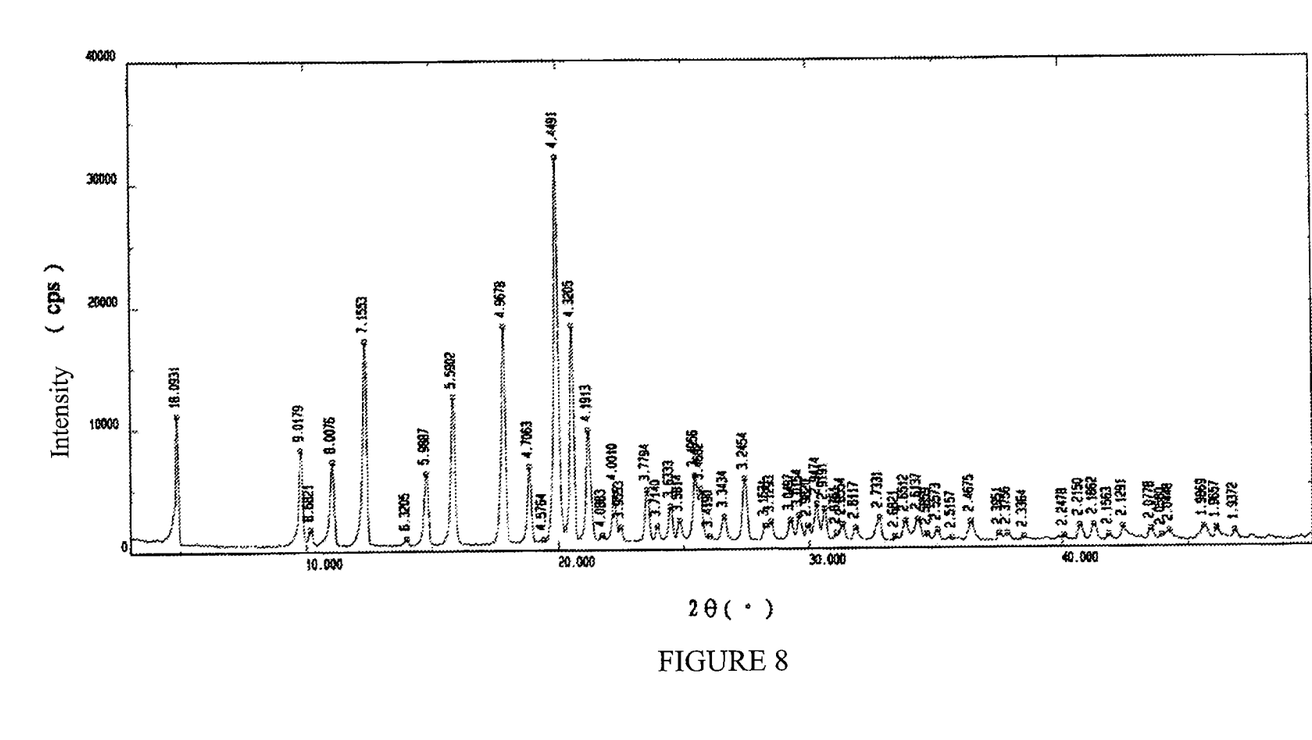
FIG. 8 presents an X-ray diffraction spectrum of the crystalline form of S-zopiclone of the present invention subjected to room temperature for 36 months.

As shown in the results of the long-term reserved-sample test, the crystalline form of S-zopiclone remained stable, and its parameters were almost consistent with those of 0th day, including character, melting point, and contents of related substances such as levozopiclone. The X-ray diffraction spectrum of the crystalline form of S-zopiclone of the present invention at room temperature for 36 months is presented in FIG. 8.

TABLE 5

Results of long-term reserved-sample test of the crystalline form of S-zopiclone

| Time (Month) | Appearance and color | Melting point (° C.) | Related substances (%) Levozopiclone | Other impurities | Content (%) |
|---|---|---|---|---|---|
| 0 | Off-white crystalline powder | 205.5~207.0 | 0.06 | 0.09 | 100.06 |
| 3 | Off-white crystalline powder | 205.0~206.5 | 0.06 | 0.11 | 100.3 |
| 6 | Off-white crystalline powder | 206.5~207.5 | 0.06 | 0.14 | 100.21 |
| 9 | Off-white crystalline powder | 206.0~207.5 | 0.04 | 0.14 | 100.16 |
| 12 | Off-white crystalline powder | 205.5~207.0 | 0.06 | 0.14 | 100.08 |
| 18 | Off-white crystalline powder | 206.0~207.5 | 0.07 | 0.17 | 100.12 |
| 24 | Off-white crystalline powder | 205.5~206.5 | 0.07 | 0.18 | 99.80 |
| 36 | Off-white crystalline powder | 206.0~207.0 | 0.07 | 0.20 | 100.06 |

Conclusions:

In summary, the crystalline form of S-zopiclone of the present invention was introduced into an open and colorless transparent weighing-bottle, and placed in different environments for 10 days, including high temperature (60° C.), relative humidity (92.5%) and strong light exposure (4500±500 Lx). In addition, after 6 months of the accelerated test of the crystalline form of S-zopiclone packaged in packages stimulated the commercial ones (temperature: 40±2° C., RH:75±5%), compared with the result on the $0^{th}$ day, no significant change was observed in many parameters, including character, melting point, and contents of related substances such as levozopiclone. The results of the influencing factors showed that the crystalline form of S-zopiclone of the present invention should be preserved in an airproof and dry place.

After 36 months of the long-term reserved-sample test of the crystalline form of S-zopiclone packaged in packages stimulated the commercial ones at room temperature, compared with the results on the $0^{th}$ day, no significant change was observed in the parameters including character, melting point, and contents of related substances such as levozopiclone.

Under the circumstances of aforesaid test, a phenomenon of crystal transformation had not been observed. It was substantially confirmed that the crystalline form of S-zopiclone of the present invention was structurally stable.

Test 3 Pharmacokinetic Study of Single Administration of the Crystalline Form of S-Zopiclone on Healthy Volunteers 1. Objective The single administration of different dosages of the drug to healthy volunteers had been investigated for evaluation of its pharmacokinetic profile, as well as the rule of in vivo distribution, metabolism and excretion. Because the crystalline form of S-zopiclone was designed to administrate to a subject in oral dosage form, the effect of eating food on adsorption, distribution, metabolism and excretion of the drug was also evaluated.

2. Method

Evaluation of pharmacokinetics: according to the results of phase I clinical tolerance trial and the pre-designed therapeutic dose of phase II clinical trial, a high dose of 11.25 mg/kg BW (body weight) can be tolerated by all volunteers in tolerance test, three different dose groups had been set as follows: low dose group, moderate dose group and high dose group were 3, 6 and 12 mg/kg BW, respectively. Three-way crossover Latin square design was used. All subjects were randomly divided into 3 test groups, and the tested drug at different doses was administrated to the subjects when performing each test. Thus, after 3 tests, each subject had been administrated with the testing drug at high, moderate and low dose by following the Latin square design procedure. The interval between two tests was 2 weeks.

In addition, the effect of eating food on in vivo metabolism of the drug had been evaluated. 8 subjects were randomly divided into 2 groups. In 2 tests, the subjects of each group received the drug at the same dose (6 mg) in the cases of fasting and 5 minutes after taking standard diet. The interval between two tests was 2 weeks.

After a single oral administration of the tested drug, 6 ml anticoagulant heparin venous blood samples were collected at 0th (immediately before administration), 15th minute, 30th minute, 45th minute, 60th minute, 1.5th hour, 2nd hour, 3rd hour, 4th hour, 6th hour, 8th hour, 12th hour, 16th hour and 24th hour respectively to determine the concentration of S-zopiclone. By HPLC, the plasma drug concentration of each subject had been determined at different time-points to give a concentration-time curve. The main pharmacokinetic parameters of the subjects had been calculated, including AUC, $C_{max}$, $T_{max}$, $AUC_{0-\alpha}$, $AUC_{0-t}$ and $t_{1/2}$, etc.

3. Selection of the Subjects

Population: (Predetermined Population and Analyzed Population) 10 Persons per Group Inclusion and exclusion criteria: aged 19~45 years and body mass index (BMI) 19~29 kg/m². The subjects' physical health was confirmed in accordance with their disease history, physical examination, ECG and laboratory test, when screening. Moreover, before the test, a written informed consent form (ICF) should be signed up.

4. Specification, Usage and Dosage of the Tested Drug

The crystalline form of S-zopiclone was prepared into coated tablets (3 mg S-zopiclone/tablet) in accordance with Example 1 and Example 9, single orally administrated.

5. Treating Duration

Twenty-four hours of observation had been made after single oral administration.

6. Evaluation Criteria

Pharmacokinetic indices: the plasma drug concentration had been determined immediately before administration and at different time-points after administration of the drug to give a concentration-time curve. The main pharmacokinetic parameters had been calculated, including $C_{max}$, $T_{max}$, $AUC_{0-\alpha}$, $AUC_{0-t}$ and $t_{1/2}$, etc.

Safety indices: a series of indices were measured when conducting screening and 24 hours after administration, including vital signs, physical examination, ECG and laboratory test. During the test, adverse event was recorded on time.

7. Statistical Method

Pharmacokinetic: 3P97 statistical analysis software had been applied to calculate the main pharmacokinetic parameters.

Safety: meaningful clinical safety indices are tabulated according to the type and the frequency thereof.

8. Results and Conclusions

The subjects obeyed the test protocol strictly without deviating or violating the protocol and without combined drugs. For non-medical reason, one of the subjects had failed to complete the last 3 blood sampling 8 hours after administration of 12 mg/kg BW drug.

Pharmacokinetic Results

The pharmacokinetic parameters of the subjects after single oral administration of crystalline form of S-zopiclone are shown in Table 6.

TABLE 6

Pharmacokinetic parameters of the subjects after single oral administration of the crystalline form of S-zopiclone

| Pharmacokinetic parameters | Pharmacokinetic study of single oral administration | | | Pharmacokinetic study pre and post eating | |
|---|---|---|---|---|---|
| | 3 mg | 6 mg | 12 mg | 6 mg (fasting) | 6 mg (eating) |
| $C_{max}$ (μg/L) | 33.96 ± 8.63 | 60.94 ± 11.44 | 182.72 ± 67.44 | 60.69 ± 11.43 | 62.60 ± 18.95 |
| $T_{max}$ (hr) | 1.50 ± 0.66 | 1.28 ± 0.43 | 1.58 ± 0.40 | 1.31 ± 0.44 | 1.75 ± 0.89 |
| $AUC_{0-\infty}$ (μg/hr/L) | 259.66 ± 92.58 | 404.21 ± 73.32 | 1291.26 ± 426.68 | 335.73 ± 145.57 | 284.00 ± 88.36 |
| $t_{1/2}$ (hr) | 6.98 ± 0.99 | 8.20 ± 6.14 | 8.06 ± 2.82 | 7.17 ± 2.69 | 6.75 ± 1.49 |
| plasma clearance (L/hr) | 14.10 ± 4.5 | 15.80 ± 3.0 | 10.90 ± 5.00 | 16.00 ± 3.3 | 21.4 ± 7.4 |

Safety Results:

Bitter taste in mouth was reported as severe adverse reaction by a majority of subjects (25%~40%), and another adverse reaction was dizziness and headache. As shown in the results, compared with the low and moderate dose groups, more types and higher frequencies of adverse reactions occurred in high dose group (12 mg/kg BW). Two subjects in the group of the dose of 12 mg/kg BW experienced the state of delirium, including talkativeness, hyperactivity and unconsciousness. But these adverse reactions were mild and had a short duration. Within 12 hours after administration, all adverse reactions disappeared without special treatment.

Conclusions:

The tablets of the crystalline form of S-zopiclone can be absorbed rapidly after oral administration. The dose and plasma drug concentration within a range of 3~12 mg had a good linear relationship. The common adverse reactions included slightly bitter taste in mouth and dizziness, indicating the crystalline form of S-zopiclone of the present invention had good safety for clinical use.

The crystalline form refers to a kind of solid substances with atoms (or ions and molecules) arranged steric-periodically. Generally, the organic drug crystalline forms belong to the molecular lattice, which can form different crystalline forms depending on different process conditions. Moreover, different crystalline forms of the same drug often cause significant differences in many physicochemical properties (for example appearance, solubility, melting point and density), drug dissolution and bioavailability, thus influencing the stability and bioavailability of the drug. By now, the researches on the polymorphism of drugs have become an indispensable and important aspect for R&D for new drugs and examination & approval, drug productions and quality controls and pre-formulation study of choosing dosage-forms for new drugs.

The crystalline form of S-zopiclone of the present invention offers advantages as follows:

1. It can provide a better therapeutical effect for treating sleep disorder, having an effect of anti-anxiety without affecting sport coordination ability.

2. It can be absorbed rapidly after oral administration. Within the range of effective dose, the dose and plasma drug concentration have a good linear relationship, making it more safety in clinical use.

3. Under the circumstances of aforesaid test, a phenomenon of crystal transformation had not been observed. It is confirmed that the crystalline form of S-zopiclone of the present invention was structurally stable.

4. It has good flowability and compressibility (e.g. easily being pressed into a tablet). On the premise of fully meeting the pharmacodynamical and pharmacokinetical requirements for clinical application, it greatly facilitates manufacturing practical preparations.

EXAMPLES

The following examples further illustrate the present invention, but not limit the invention by any means.

Preparative Example

Preparation of S-Zopiclone as a Raw Material

Racemic zopiclone (100 g), D-(+)-malic acid (34 g), methanol (1000 mL) and acetone (1500 mL) were added into 3 L reaction flask to dissolve under agitation for 2 hours at room temperature. The obtained solution was allowed to cool down to 6° C. After about 24 hours at 6° C., the solution was agitated for 1 hour, filtered, washed with methanol twice (a total volume of 100 mL) and dried to obtain D-(+)-malic acid-S-zopiclone (52.5 g).

Aforesaid D-(+)-malic acid-S-zopiclone (52.5 g) was dissolved in water (1000 mL), followed by addition of potassium bicarbonate (8%) to adjust pH value to 8, and solid substance was precipitated. Then the solution was extracted with ethyl acetate for 4 times (a total volume of 1000 mL). The ethyl acetate layer was dried with anhydrous sodium sulfate (as a desiccant) for 5 hours, filtered and the desiccant was removed. The solution was concentrated by distillation, then filtered, washed with ethyl acetate for 3 times (a total volume of 100 mL) and dried to give S-zopiclone (33.2 g) as a raw material.

Example 1

Preparation of the Crystalline Form of S-Zopiclone

S-zopiclone (10.0 g) was added into a 500 mL flask. Ethyl acetate (350 mL) was added, agitated, heated to make solid substance gradually dissolved. The obtained solution was refluxed for 10 minutes and allowed to cool down at ambient temperature to about 40° C. After 2 hours of agitation at about 40° C., the solution was cooled down to about 0° C., agitated for 1 hour at about 0° C., filtered by suction and dried in vacuum to obtain the crystalline form of S-zopiclone (8.9 g). Identified by the Following Data:

Powder X-ray diffraction spectrum showed characteristic peaks expressed in terms of 2θ at about 11.08°, about 12.38°, about 15.86°, about 17.88°, about 19.98° and about 20.58°. The peak in DSC thermogram was at about 207.7° C.

Infrared absorption spectrum (IR) showed characteristic peaks at about 3078 $cm^{-1}$, about 2942~2838 $cm^{-1}$, about 2790 $cm^{-1}$, about 1715 $cm^{-1}$, about 1463 $cm^{-1}$, about 1372 $cm^{-1}$ and about 757 $cm^{-1}$.

Example 2

Preparation of the Crystalline form of S-Zopiclone

S-zopiclone (10.0 g) was added into a 500 mL flask. Ethyl acetate (250 mL) was added, agitated, heated to make solid substance gradually dissolved. The obtained solution was refluxed for 10 minutes and allowed to cool down at ambient temperature to about 45° C. After 10 minutes of agitation at about 45° C., the solution was cooled down to about 1° C., agitated for 2 hours about 1° C., filtered by suction and dried in vacuum to obtain the crystalline form of S-zopiclone (9.0 g).

Identified by the Following Data:

Powder X-ray diffraction spectrum showed characteristic peaks expressed in terms of 2θ at about 11.15°, about 12.38°, about 15.92°, about 17.79°, about 19.93° and about 20.52°. The peak in DSC thermogram was at about 208.4° C.

Infrared absorption spectrum (IR) showed characteristic peaks at about 3081 $cm^{-1}$, about 2941~2838 $cm^{-1}$, about 2791 $cm^{-1}$, about 1716 $cm^{-1}$, about 1463 $cm^{-1}$, about 1372 $cm^{-1}$ and about 758 $cm^{-1}$.

Example 3

Preparation of the Crystalline Form of S-Zopiclone

S-zopiclone (10.0 g) was added into a 1000 mL flask. Ethyl acetate (500 mL) was added, agitated, heated to make solid substance gradually dissolved. The obtained solution was refluxed for 10 minutes and allowed to cool down at ambient temperature to about 35° C. After 7 hours of agitation at about 35° C., the solution was cooled down to about 3° C., agitated for 5 hours at about 3° C., filtered by suction and dried in vacuum to obtain the crystalline form of S-zopiclone (8.7 g). Identified by the Following Data:

Powder X-Ray diffraction spectrum showed characteristic peaks expressed in terms of 2θ at about 11.08°, about 12.42°, about 15.87°, about 17.81°, about 19.9° and about 20.55°. The peak in DSC thermogram was at about 207.3° C.

Infrared absorption spectrum (IR) showed characteristic peaks at about 3077 cm$^{-1}$, about 2942~2839 cm$^{-1}$, about 2791 cm$^{-1}$, about 1714 cm$^{-1}$, about 1463 cm$^{-1}$, about 1372 cm$^{-1}$ and about 757 cm$^{-1}$.

Example 4

Preparation of the Crystalline Form of S-Zopiclone

S-zopiclone (10.0 g) was added into a 250 mL flask. Ethyl acetate (100 mL) was added, agitated, heated to make solid substance gradually dissolved. The obtained solution was refluxed for 10 minutes and allowed to cool down at ambient temperature to about 50° C. After 4 hours of agitation at about 50° C., the solution was cooled down to about 8° C., agitated for 7 hours at about 8° C., filtered by suction and dried in vacuum to obtain the crystalline form of S-zopiclone (9.2 g). Identified by the Following Data:

Powder X-ray diffraction spectrum showed characteristic peaks expressed in terms of 2θ at about 11.08°, about 12.38°, about 15.86°, about 17.85°, about 19.9° and about 20.58°. The peak in DSC thermogram was at about 207.2° C.

Infrared absorption spectrum (IR) showed characteristic peaks at about 3077 cm$^{-1}$, about 2941~2837 cm$^{-1}$, about 2792 cm$^{-1}$, about 1715 cm$^{-1}$, about 1463 cm$^{-1}$, about 1372 cm$^{-1}$ and about 758 cm$^{-1}$.

Example 5

Preparation of the Crystalline Form of S-Zopiclone

S-zopiclone (10.0 g) was added into a 1000 mL flask. Ethyl acetate (800 mL) was added, agitated, heated to make solid substance gradually dissolved. The obtained solution was refluxed for 10 minutes and allowed to cool down at ambient temperature to about 30° C. After 10 hours of agitation at about 30° C., the solution was cooled down to about −5° C., agitated for 50 minutes at about -5° C., filtered by suction and dried in vacuum to obtain the crystalline form of S-zopiclone (8.4 g).
Identified by the Following Data:

Powder X-ray diffraction spectrum showed characteristic peaks expressed in terms of 2θ at about 11.07°, about 12.35°, about 15.86°, about 17.88°, about 19.94° and about 20.58°. The peak in DSC thermogram was at about 208.1° C.

Infrared absorption spectrum (IR) showed characteristic peaks at about 3077 cm$^{-1}$, about 2943~2839 cm$^{-1}$, about 2791 cm$^{-1}$, about 1715 cm$^{-1}$, about 1463 cm$^{-1}$, about 1371 cm$^{-1}$ and about 757 cm$^{-1}$.

Example 6

Preparation of the Crystalline Form of S-Zopiclone

S-zopiclone (10.0 g) was added into a 1000 mL flask. Ethyl acetate (750 mL) was added, agitated, heated to make solid substance gradually dissolved. The obtained solution was refluxed for 10 minutes and allowed to cool down at ambient temperature to about 45° C. After 10 minutes of agitation at about 45° C., the solution was cooled down to about 0° C., agitated for 2 hours at about 0° C., filtered by suction and dried in vacuum to obtain the crystalline form of S-zopiclone (8.8 g).
Identified by the Following Data:

Powder X-ray diffraction spectrum showed characteristic peaks expressed in terms of 2θ at about 11.08°, about 12.38°, about 15.86°, about 17.86°, about 19.98° and about 20.58°.

The peak in DSC thermogram was at about 207.5° C.

Infrared absorption spectrum (IR) showed characteristic peaks at about 3078 cm$^{-1}$, about 2942~2838 cm$^{-1}$, about 2790 cm$^{-1}$, about 1717 cm$^{-1}$, about 1463 cm$^{-1}$, about 1371 cm$^{-1}$ and about 759 cm$^{-1}$.

Example 7

Preparation of the Crystalline Form of S-Zopiclone

S-zopiclone (10.0 g) was added into a 500 mL flask. Ethyl acetate (400 mL) was added, agitated, heated to make solid substance gradually dissolved. The obtained solution was refluxed for 10 minutes and allowed to cool down at ambient temperature to about 35° C. After 12 hours of agitation at about 35° C., the solution was cooled down to about -10° C., agitated for 10 minutes at about -10° C., filtered by suction and dried in vacuum to obtain the crystalline form of S-zopiclone (8.3 g).
Identified by the Following Data:

Powder X-ray diffraction spectrum showed characteristic peaks expressed in terms of 2θ at about 11.08°, about 12.34°, about 15.92°, about 17.88°, about 19.98° and about 20.58°.

The peak in DSC thermogram was at about 207.7° C.

Infrared absorption spectrum (IR) showed characteristic peaks at about 3078 cm$^{-1}$, about 2941~2837 cm$^{-}$, about 2790 cm$^{-1}$, about 1715 cm$^{-1}$, about 1464 cm$^{-1}$, about 1372 cm$^{-1}$ and about 757 cm$^{-1}$.

Example 8

Preparation of the Crystalline Form of S-Zopiclone

S-zopiclone (10.0 g) was added into a 1000 mL flask. Ethyl acetate (700 mL) was added, agitated, heated to make solid substance gradually dissolved. The obtained solution was refluxed for 10 minutes and allowed to cool down at ambient temperature to about 38° C. After 12 hours of agitation at about 38° C., the solution was cooled down to about 10° C., agitated for 12 hours at about 10° C., filtered by suction and dried in vacuum to obtain the crystalline form of S-zopiclone (8.9 g).
Identified by the Following Data:

Powder X-ray diffraction spectrum showed characteristic peaks expressed in terms of 2θ at about 11.08°, about 12.41°, about 15.86°, about 17.81°, about 19.98° and about 20.58°.

The peak in DSC thermogram was at about 207.6° C.

Infrared absorption spectrum (IR) showed characteristic peaks at about 3081 cm$^{-1}$, about 2943~2838 cm$^{-1}$, about 2790 cm$^{-1}$, about 1715 cm$^{-1}$, about 1466 cm$^{-1}$, about 1372 cm$^{-1}$ and about 757 cm$^{-1}$.

Example 9

Preparation Tablets of the Crystalline Form of S-Zopiclone

Formula

| Components | Weight (g) |
|---|---|
| The crystalline form of S-zopiclone | 30.00 |
| Lactose | 500.00 |
| Corn starch | 100.00 |
| Pre-gelatinized starch | 50.00 |
| Povidone K30 | 10.00 |
| Sodium carboxymethyl starch | 30.00 |
| Micropowder silica gel | 3.00 |
| Magnesium stearate | 4.00 |
| Povidone K30 aqueous solution (8%) | Proper amount |
| Opadry II coating agent | 20.00 |

Ten thousands of tablets were prepared, and each tablet contains 3 mg of the crystalline form of S-zopiclone of the present invention.

The specific operation steps are as follows: the crystalline form of S-zopiclone, lactose, corn starch, pre-gelatinized starch, povidone K30, sodium carboxymethyl starch and micropowder silica gel were passed through a 100-mesh sieve respectively for later use. The crystalline form of S-zopiclone was weighed according to the amount as described in the formula and mixed homogeneously with other adjuvants in a manner of progressively increasing in equal amount. The mixture was passed through a 100-mesh sieve for 3 times. A proper amount of povidone K30 aqueous solution (8%) was added into the obtained powder to make soft-material. The soft-material was granulated by passing through a 20-mesh sieve. The wetted granules were dried at 50~60° C. and passed through a 20-mesh sieve until uniform granules were obtained. Micropowder silica gel was added and well blended. Then magnesium stearate was added and well mixed. The angle of repose was measured as less than 30°. The content of the drug was tested and the weight of the tablets was determined, and then the tablets were prepared by using a 6 mm flat punch for later coating.

The obtained plain tablets were coated with Opadry® II coating agent. According to conventional formula of Opadry® II (stomach-soluble type), a coating solution was prepared by using water as a solvent. The solid content of the coating solution was 18%. Inlet air temperature: 80° C., Fluidizing bed temperature: 38~40° C., Atomization pressure: 3.5 Bar, Rotary speed of the coating vessel: 23 rpm, Feeding flow rate: 2~3 g/minute. Formed coating membrane had high strength, strong adhesive force, complete covering and uniform color.

The tablets were administrated to the patient about 1 hour before sleep, single oral administration at a dose of 1~4 tablets.

Example 10

Preparation of Capsules of the Crystalline Form of S-Zopiclone

Formula

| Components | Weight (g) |
|---|---|
| The crystalline form of S-zopiclone | 30.00 |
| Lactose | 500.00 |
| Corn starch | 100.00 |
| Pre-gelatinized starch | 50.00 |
| Povidone K30 | 10.00 |
| Sodium carboxymethyl starch | 30.00 |
| Micropowder silica gel | 3.00 |
| Magnesium stearate | 4.00 |
| Povidone K30 aqueous solution (8%) | Proper amount |

Ten thousands of capsules were prepared, and each capsule contains 3 mg of the crystalline form of S-zopiclone.

The specific operation steps are as follows: the crystalline form of S-zopiclone, lactose, corn starch, pre-gelatinized starch, povidone K30, sodium carboxymethyl starch and micropowder silica gel were passed through a 100-mesh sieve respectively for later use. The crystalline form of S-zopiclone was weighed according to the amount as described in the formula and mixed homogeneously with other adjuvants in a manner of progressively increasing in equal amount. The mixture was passed through a 100-mesh sieve for 3 times. A proper amount of povidone K30 aqueous solution (8%) was added into the obtained powder to make soft-material. The soft-material was granulated by passing through a 20-mesh sieve. The wetted granules were dried at 50~60° C. and passed through a 20-mesh sieve until uniform granules were obtained. Micropowder silica gel was added and well blended. Then magnesium stearate was added and well mixed. The angle of repose was measured as less than 30°. After the content of the drug was tested, then a loading capacity was determined.

Capsules were prepared by loading into No. 3 capsules.

The capsules were administrated to the patient about 1 hour before sleep, single oral administration at a dose of 1~4 capsules.

The invention claimed is:

1. A crystalline form of (S)-zopiclone having a powder X-ray diffraction pattern with characteristic peaks expressed in terms of 2θ at 11.08°, 12.38°, 15.86°, 17.88°, 19.98° and 20.58°; a differential scanning calormetry thermogram with a peak at 207.7° C. and an infrared absorption spectrum (IR) with characteristic peaks at 3078 $cm^{-1}$, 2942 to 2838 $cm^{-1}$, 2790 $cm^{-1}$, 1716 $cm^{-1}$, 1463 $cm^{-1}$, 1372 $cm^{-1}$ and 757 $cm^{-1}$.

2. A process for preparing the crystalline form of (S)-zopiclone of claim 1, the process comprises the following steps:
   (a). dissolving (S)-zopiclone in ethyl acetate at a temperature ranging from 60° C. to a reflux temperature, wherein the ratio of the volume of ethyl acetate to the weight of (S)-zopiclone is from 10 mL 80 mL of ethyl acetate to 1 gram of (S)-zopiclone;
   (b). allowing the solution to cool down to a temperature ranging from 30° C. to 50° C.;
   (c). maintaining the solution at the temperature ranging from 30° C. to 50° C. for a period of 10 minutes to 12 hours;

(d). further cooling the solution to a temperature ranging from 10° C. to −10° C.;

(e). maintaining the solution at the temperature ranging from 10° C. to −10° C. for a period of 10 minutes to 12 hours; and (f). isolating the crystalline form of (S)-zopiclone of claim 1.

3. The process according to claim 2, wherein in step (a), the ratio of the volume of ethyl acetate to the weight of (S)-zopiclone is from 25 mL to 50 mL of ethyl acetate to 1 gram of (S)-zopiclone; in step (b), the solution is allowed to cool to a temperature ranging from 35° C. to 45° C.; in step (c), the solution is maintained at the temperature ranging from 35° C. to 45° C. for a period of 1 hour to 6 hours; in step (d), the solution is further cooled to a temperature ranging from 5° C. to −5° C.; and in step (e), the solution is maintained at the temperature ranging from 5° C. to −5° C. for a period of 1 hour to 6 hours.

4. A pharmaceutical composition comprising the crystalline form of (S)-zopiclone of claim 1 and a pharmaceutically acceptable carrier.

5. The pharmaceutical composition according to claim 4, wherein one dosage unit of the pharmaceutical composition contains 1-15 mg of the crystalline form of (S)-zopiclone.

6. The pharmaceutical composition according to claim 5, wherein one dosage unit of the pharmaceutical composition contains 3-12 mg of the crystalline form of (S)-zopiclone.

7. A method for treating sleep disorders, wherein the method comprises administering a therapeutically effective amount of the crystalline form of (S)-zopiclone of claim 1 to a subject in need thereof.

8. A method for treating sleep disorders, wherein the method comprises administering a therapeutically effective amount of any one of the pharmaceutical compositions of claims 4-6 to a subject in need thereof.

* * * * *

UNITED STATES PATENT AND TRADEMARK OFFICE
CERTIFICATE OF CORRECTION

PATENT NO. : 8,431,577 B2  
APPLICATION NO. : 12/999867  
DATED : April 30, 2013  
INVENTOR(S) : Guocheng Wang et al.

Page 1 of 1

It is certified that error appears in the above-identified patent and that said Letters Patent is hereby corrected as shown below:

<u>On the Title Page, Item (54) and in the Specification, Column 1</u>

In the Title, before "COMPOSITION," insert --ITS--.

<u>In the Claims</u>

In column 18, claim 2, line 56, after "of claim 1," replace "the process" with --which--.

In column 18, claim 2, line 61, replace "10 mL 80 mL" with --10 mL to 80 mL--.

In column 18, claim 2, line 63, after "solution to cool" delete "down".

Signed and Sealed this
Twenty-sixth Day of August, 2014

Michelle K. Lee
*Deputy Director of the United States Patent and Trademark Office*